(12) United States Patent
Winstrom

(10) Patent No.: US 11,547,862 B2
(45) Date of Patent: Jan. 10, 2023

(54) WIRELESS POWER TRANSFER CIRCUIT FOR A RECHARGEABLE IMPLANTABLE PULSE GENERATOR

(71) Applicant: ADVANCED NEUROMODULATION SYSTEMS, INC., Plano, TX (US)

(72) Inventor: William Winstrom, Leander, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 490 days.

(21) Appl. No.: 16/676,197

(22) Filed: Nov. 6, 2019

(65) Prior Publication Data
US 2020/0324126 A1 Oct. 15, 2020

Related U.S. Application Data

(60) Provisional application No. 62/834,221, filed on Apr. 15, 2019.

(51) Int. Cl.
*A61N 1/378* (2006.01)
*A61N 1/372* (2006.01)

(52) U.S. Cl.
CPC ....... *A61N 1/3787* (2013.01); *A61N 1/37229* (2013.01)

(58) Field of Classification Search
CPC .............. A61N 1/3787; A61N 1/37229; A61N 1/0534; A61N 1/0543; A61N 1/0551; A61N 1/36007; A61N 1/36062; A61N 1/362; H02J 50/005; H02J 50/12; H02J 50/80
See application file for complete search history.

(56) References Cited

U.S. PATENT DOCUMENTS

| 4,392,087 | A | * | 7/1983 | Zansky | .............. | H05B 41/2985 315/225 |
| 5,702,431 | A | | 12/1997 | Wang et al. | | |
| 6,163,723 | A | * | 12/2000 | Roberts | .............. | A61N 1/36585 607/18 |
| 6,442,434 | B1 | * | 8/2002 | Zarinetchi | ............... | H02J 50/90 607/33 |
| 7,212,110 | B1 | | 5/2007 | Martin et al. | | |

(Continued)

FOREIGN PATENT DOCUMENTS

EP 1609501 A1 12/2005

OTHER PUBLICATIONS

Davis, S., Power Management Chapter 12: Wireless Power Transfer, Power Electronics, Jun. 28, 2018, 15 pgs.

(Continued)

*Primary Examiner* — Catherine M Voorhees
(74) *Attorney, Agent, or Firm* — The Small Patent Law Group LLC; Dean D. Small

(57) ABSTRACT

A charging energy control system includes an implantable medical device (IMD) and an external charger for effectuating wireless power transfer. The IMD receives charging energy to recharge a battery during an ON period and rejects the charging energy during an OFF period. A series switch is disposed between the IMD's coil and rectifier circuitry that is controlled by voltage regulation circuitry operative to generate a clamp control signal configured to detune the coil in the OFF state.

22 Claims, 8 Drawing Sheets

(56) References Cited

U.S. PATENT DOCUMENTS

| | | | |
|---|---|---|---|
| 7,571,007 B2* | 8/2009 | Erickson | A61N 1/3787 607/61 |
| 8,731,682 B2* | 5/2014 | Winstrom | A61N 1/3787 607/61 |
| 9,142,989 B2 | 9/2015 | Fell et al. | |
| 9,270,137 B2 | 2/2016 | Greene | |
| 2015/0306407 A1* | 10/2015 | Crutchfield | A61N 1/3912 607/5 |
| 2019/0168005 A1* | 6/2019 | Li | A61N 1/37229 |
| 2020/0324126 A1 | 10/2020 | Winstrom et al. | |

OTHER PUBLICATIONS

International Preliminary Report on Patentability for corresponding Application No. PCT/US2020/059299 dated May 19, 2022.

* cited by examiner

WIRELESS POWER TRANSFER CIRCUIT FOR A RECHARGEABLE IMPLANTABLE PULSE GENERATOR

PRIORITY AND CROSS-REFERENCE TO RELATED APPLICATION(S)

This patent application claims the benefit of the following prior United States provisional patent application(s): (i) "WIRELESS POWER TRANSFER CIRCUIT FOR A RECHARGEABLE IMPLANTABLE PULSE GENERATOR," Application No. 62/834,221, filed Apr. 15, 2019, in the name(s) of William Winstrom, each of which is hereby incorporated by reference in its entirety.

TECHNICAL FIELD

The present disclosure generally relates to implantable medical devices, and more particularly to a system and method for controlling charging energy delivered to an implantable medical device using wireless power transfer.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include deep brain stimulation, cortical stimulation, cochlear nerve stimulation, peripheral nerve stimulation, vagal nerve stimulation, sacral nerve stimulation, etc.

In addition to neurostimulation (NS) systems, several numerous medical devices exist today, including but not limited to electrocardiographs (ECGs), electroencephalographs (EEGs), squid magnetometers, implantable pacemakers, implantable cardioverter-defibrillators (ICDs), electrophysiology (EP) mapping and radio frequency (RF) ablation systems, and the like, that may be implanted within a patient for facilitating therapy and/or diagnostics. In general, implantable medical devices or IMDs are configured to be implanted within patient anatomy and commonly employ one or more leads with electrodes that either receive or deliver voltage, current or other electromagnetic pulses from or to an organ or tissue for diagnostic or therapeutic purposes.

In order to provide consistent therapy and reliable operation over a substantial duration of time, IMDs are often provided with one or more batteries that may be charged and recharged to store energy, which may supply power to the rest of the IMD circuitry and associated lead systems. Because IMDs are implanted within patients, the IMDs are typically charged by an external charger that transmits energy wirelessly into the IMDs, such as through radio frequency (RF) signals. It is desirable that an IMD is generally charged as quickly and safely as possible within certain ranges depending upon the therapy application. However, if charging energy is input into the IMD too quickly and/or without proper regulation, the temperature of the IMD may increase to dangerous levels causing tissue damage and other deleterious effects. It is further desired that wireless energy transfer between the external charger and the IMD's charging circuitry be performed as efficiently as possible.

Whereas advances in IMD technologies and associated external charger systems continue to grow apace, several lacunae remain, thereby requiring further innovation as will be set forth hereinbelow

SUMMARY

Embodiments of the present patent disclosure are broadly directed to a wireless charging energy control system that includes an implantable medical device (IMD) and an external charger for effectuating wireless power transfer. In one arrangement, the IMD may be configured to receive charging energy to (re)charge a battery during an ON period and to reject the charging energy during an OFF period. A series switch may be disposed between the IMD's coil and rectifier circuitry that is controlled by voltage regulation circuitry operative to generate a clamp control signal configured to detune the coil in the OFF state. In one arrangement, the series switch may be disposed in a circuit configuration that advantageously facilitates electrical contact between the coil and rectifier circuitry using only a minimum number of feedthrough paths effectuated via a suitable electromechanical interface (e.g., a "header" portion of the IMD).

In one aspect, an embodiment of the present patent disclosure is directed to an IMD configured to provide stimulation therapy to a patient, wherein the IMD is operative receive wireless RF power for (re)charging a battery therein. The IMD may comprise, inter alia, a rechargeable battery, pulse generating circuitry powered by the rechargeable battery, and an inductive coupling element including at least one inductor (L) and at least one capacitor (C) coupled to the at least one inductor in a series LC circuit configuration operative to accept RF power from an external charger. In one implementation, the series LC circuit configuration may be arranged such that a first electrical node is formed or defined at a terminal of the at the least one inductor and a second electrical node is formed or defined at a terminal of the at least one capacitor. A series switch is disposed between the first electrical node of the series LC circuit configuration and a bridge rectifier operative to generate a charging voltage at an output node of the bridge rectifier from an induced voltage/current provided by the inductive coupling element when magnetically coupled to the external charger to receive the RC power. The IMD may further include voltage regulation circuitry operative to regulate a level of the charging voltage generated at the output node of the bridge rectifier for charging the rechargeable battery as well as a coil clamp control circuit operative in association with the voltage regulation circuitry to detune the inductive coupling element by controlling the series switch in an OFF state. The voltage regulation circuitry and the coil clamp control circuit may be arranged to generate appropriate control signals to drive the series switch so as to prevent a high voltage condition from developing in the series LC circuit configuration that may be caused due to resonance in the OFF state.

In another aspect, an embodiment of the present patent disclosure is directed to a method of charging an IMD implanted within a patient for providing stimulation therapy and/or diagnostics. The method may comprise, inter alia, positioning an external charger proximate to the patient for effectuating a near field coupling relationship with the IMD, wherein the external charger includes a primary coil and the IMD includes a secondary coil, and selecting one or more charging parameters for driving the primary coil to generate RF power at a particular frequency, the RF power operating to induce a voltage/current across the secondary coil of the IMD. The induced voltage may be converted to a charging voltage by a bridge rectifier of the IMD. The method may further include detecting clamping of the secondary coil due to at least one of: (i) detuning the secondary coil caused by opening a series switch disposed between the bridge rectifier and the secondary coil, and (ii) assertion of a voltage clamp control signal generated responsive to monitoring a target voltage level of the charging voltage generated by the bridge rectifier. In one variation, an over-voltage protection level may also be monitored to generate a clamp control signal. The external charger may monitor a rate of occurrence of clamping at the secondary coil of the IMD, and responsive thereto, the frequency of RF power generated by the primary coil of the external charger may be modified. In one embodiment, the rate of occurrence of clamping may be monitored over a select or otherwise defined period of time. In one embodiment, the frequency of the RF source may be increased so as to cause a reduction in the applied RF power responsive to determining that the rate of occurrence of clamping over the defined period of time is greater than a predetermined threshold. In one embodiment, the frequency of the RF source may be reduced so as to cause an increase in the applied RF power responsive to determining that the rate of occurrence of clamping over the defined period of time is less than a predetermined threshold.

In a still further aspect, an embodiment of a biostimulation system is disclosed, which comprises, inter alia, an IMD implanted within a patient to provide stimulation therapy to a specific tissue of the patient, the IMD comprising a rechargeable battery and pulse generating circuitry powered by the rechargeable battery; and an external charger including a primary coil configured to effectuate a near field coupling relationship with the IMD via when positioned proximate to a region of the patient having the IMD. A series switch may be disposed between the IMD's tuning portion comprising a secondary coil and internal rectifier and voltage charge regulation circuitry. In one arrangement, the IMD's tuning portion may be disposed in a header portion that is hermetically coupled to a body that houses the internal rectifier and charge regulation circuitry. The series switch may comprise a transistor device controlled by the voltage charge regulation circuitry operative to generate a clamp control signal configured to detune the secondary coil in an OFF state while facilitating a electrical contact between the IMD's tuning portion and the internal rectifier/regulation circuitry using a minimum number of feed-throughs, e.g., two feedthrough paths, facilitated via the header portion associated with the IMD's body.

Additional/alternative features, variations and/or advantages of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

DETAILED DESCRIPTION

Figure 1:
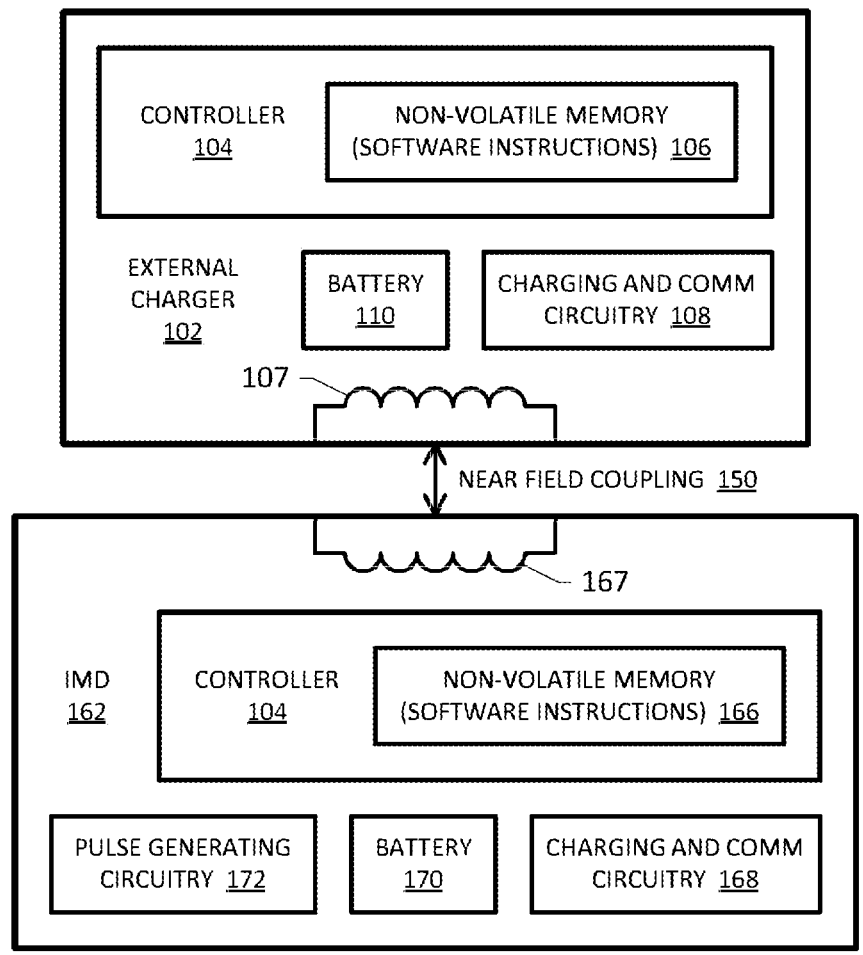
FIG. 1 depicts block diagrams of an external charging system and an implantable medical device (IMD) having wireless power transfer circuitry according to an embodiment.

In the description herein for embodiments of the present disclosure, numerous specific details are provided, such as examples of circuits, devices, components, and/or methods, etc., to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth with respect to an implantable pulse generator (IPG) configured for generating electrical stimulation for application to a desired area of a body or tissue based on a suitable stimulation therapy application, such as a spinal cord stimulation (SCS) system. However, it should be understood that example wireless power transfer circuitry and methods of operation disclosed herein are not limited thereto, but have broad applicability, including but not limited to different types of implantable devices such as neuromuscular stimulators and sensors, dorsal root ganglion (DRG) stimulators, deep brain stimulator (DBS) devices, cochlear stimulators, retinal implanters, drug delivery systems, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG or IMD. For example, some embodiments may be implemented with respect to a fully implantable pulse generator, a radio frequency (RF) pulse generator, an external pulse generator, a micro-implantable pulse generator, inter alia.

Figure 9:
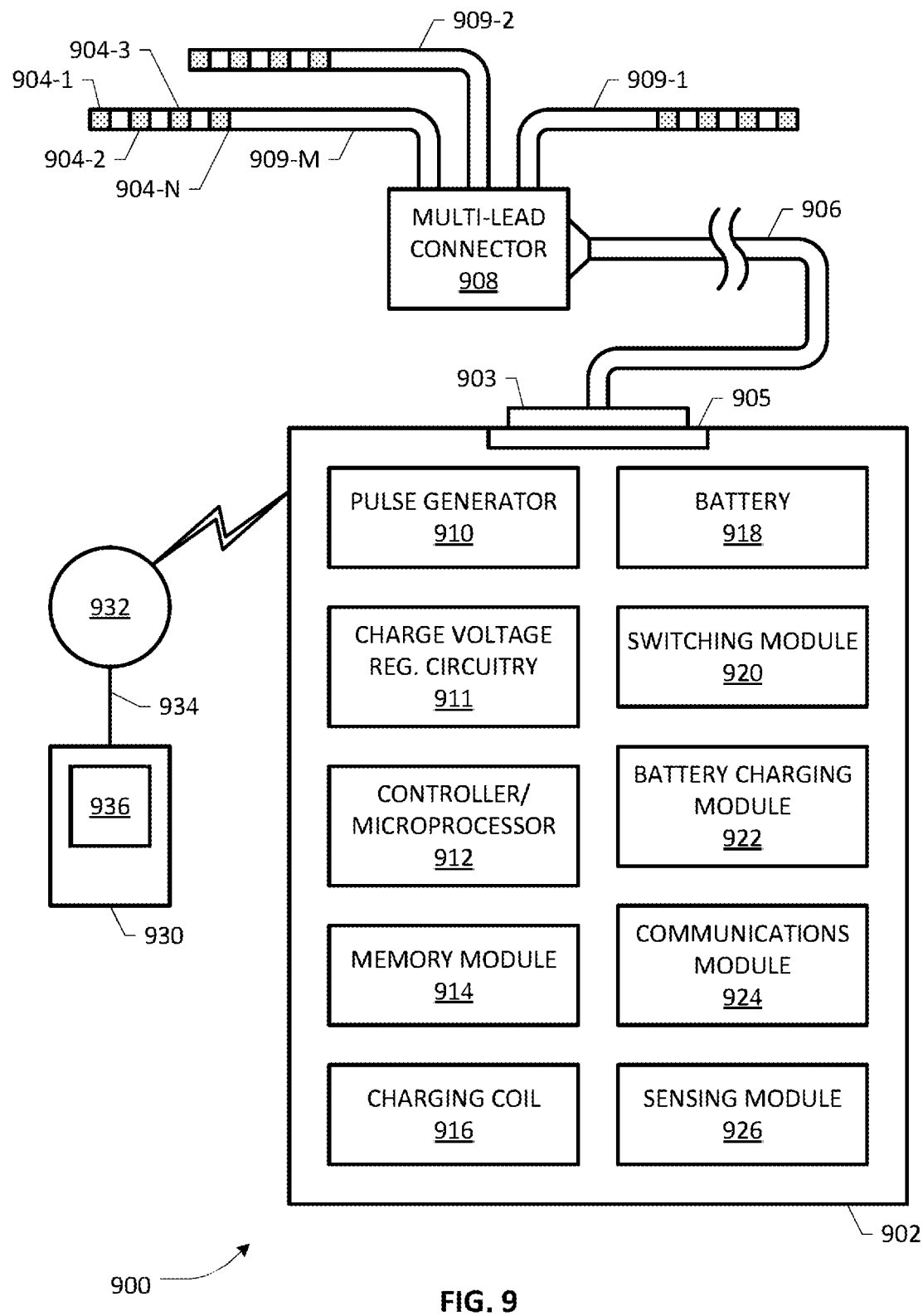
FIG. 9 depicts an IMD charging system having wireless transfer circuitry according to an example embodiment of the present disclosure.

Referring to FIG. 9 in particular, depicted therein is a biostimulation system 900 wherein one or more embodiments the present disclosure may be practiced in association with an IPG/IMD for achieving optimized wireless power transfer from an external charging system according to the teachings herein. By way of illustration, system 900 may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 900 comprises IMD 902 having a pulse generator portion that is adapted to include or otherwise interoperate with (re)chargeable battery circuitry for generating suitable stimulation pulses having adjustable target voltages that may be selectively applied for purposes of therapy. As will be set forth below in additional detail hereinbelow, IMD 902 may be implemented in one example embodiment as having a metallic housing or can that encloses a controller/processing block or module 912, pulse generating circuitry 910, charging voltage regulation module 911, a charging coil 916, a battery 918, a far-field and/or near field communication block or module 924, battery charging circuitry 922, switching circuitry 920, sensing circuitry 926, one or more memory modules 914, and the like. Controller/processor module 912 typically includes a microcontroller or other suitable processor for controlling the various other components of IMD 902. Software/firmware code may be stored in memory 914, which may be integrated with the controller/processor module 912, and/or other suitable application-specific storage components (not particularly shown in this FIG.) for execution by the microcontroller or processor 912 and/or other programmable logic blocks to control the various components of IMD 902 for purposes of an embodiment of the present patent disclosure.

In one arrangement, IMD 902 may be configured to couple to one or more stimulation leads 909-1 to 909-M using an implantable multi-lead connector 908 operative to receive corresponding stimulation leads 909-1 to 909-M at their respective proximal ends for securely engaging and providing electrical connectivity with respect to each stimulation lead's distal end having a plurality of stimulation electrodes. By way of illustration, stimulation lead 909-M is exemplified with stimulation electrodes 904-1 to 904-N, which may be implanted near or adjacent to the patient's target tissue. Stimulation leads 909-1 to 909-M may comprise percutaneous leads, paddle leads, etc., wherein the electrodes may comprise ring electrodes, segmented or split electrodes, planar electrodes, and the like, that may be energized by the pulse generating circuitry 910 according to applicable therapy protocols/regimes. Preferably, a single lead cable 906 may be provided for electrically connecting the multi-lead connector 908 to IPG 902 via a suitable connector interface or socket 903 that may be mated to an interface receptacle or header portion 905 of IMD 902. In general operation, electrical pulses may generated by the pulse generating circuitry 910 under the control of processing block 912, which may be provided to the switching circuitry 920 that is operative to selectively connect to the electrical outputs of the IMD, which are ultimately coupled to one or more electrodes of any combination of leads 904-1 to 904-M at a distal end of the lead system via respective electrical conductive traces An external device 930 may be implemented to charge/recharge the battery 918 of IMD 902, to access memory 914, and/or to program or reprogram IMD 902 with respect to the stimulation set parameters including pulsing specifications while implanted within the patient (although a separate recharging device could alternatively be employed). In alternative embodiments, accordingly, separate programmer and charger devices may be employed for charging and/or programming IMD 902 and/or any programmable components thereof. Regardless of whether charging functionalities and communication/programming functionalities are integrated, an example embodiment of the external device 930 may be a processor-based system that possesses wireline and/or wireless communication capabilities, near field magnetic/RF coupling capabilities, etc. Software may be stored within a non-transitory memory of the external device 930, which may be executed by the processor 936 to control the various operations of the external device 930. A connector or "wand" 934 may be electrically coupled to the external device 930 through suitable electrical connectors (not specifically shown), which may be electrically connected to a telemetry/charging component 932 (e.g., inductor coil, RF transceiver, etc.) at the distal end of wand 934 through respective links that allow bi-directional communication with IMD 902. Optionally, in some embodiments, wand 934 may comprise one or more temperature sensors for use during charging operations.

Turning attention now to FIG. 1, depicted therein is a block diagram of charging system 100 comprising an external charger 102 and an IPG device 162 that includes an embodiment of wireless power transfer circuitry according to the teachings herein. For purposes of the present patent disclosure, example IPG 162 may comprise any of the IMDs having any number or type of lead systems set forth above. Accordingly, the terms "IMD", "IPG", or related terms of similar import will be somewhat synonymously used in the patent application. In one arrangement, charger 102 may include a controller or processor 104 (e.g., any suitable commercially available microcontroller) for controlling the operations of charger 102 according to instructions stored in non-volatile memory 106. In one arrangement, charger 102 may be powered by a battery 110 having a suitable output voltage range. In some embodiments, battery 110 may comprise a rechargeable Lithium (Li) ion battery although other battery types or chemistries may be used. In some further embodiments, inductive step-up converters may be used in conjunction with a battery to obtain a suitable coil drive voltage. External charger 102 also comprises charging and communication circuitry 108, which may be adapted or otherwise configured in some embodiments to electrically couple to a coil 107 operating as a charging energy source. In some embodiments, coil 107 may be disposed in an external wand (not shown in this FIG.) that may be held, during charging, by a patient or an authorized healthcare professional about the patient's body adjacent to an implant site of IMD 162. Alternatively, the charger's coil 107 (which may be referred to as a primary coil) may be integrated in the same device package with the circuitry of charger 110. Preferably, charging and communication circuitry 108 may be configured to drive the primary coil 107 using a suitable RF signal for charging purposes. In some arrangements, charging and communication circuitry 108 may also drive the coil 107 using a suitable modulated RF signal to communicate/receive data to/from IMD 162. In still further embodiments, charger 102 may also be adapted for use as a controller to control the operations of IPG 162 by communicating suitable control parameters using circuitry 108, as noted above.

Example IMD 162, which is another representation of IMD 902 described above, is illustrated herein as comprising controller 164 (e.g., any suitable commercially available microcontroller) for controlling the pulse generation functionalities and other operations of IMD 162 according to instructions stored in non-volatile memory 166. IMD 162 comprises pulse generating circuitry 172 for generating stimulation pulses for delivery to tissue of the patient. It should be appreciated that any suitable existing or later developed pulse generating circuitry may be employed. An example of pulse generating circuitry is described in U.S. Patent Application Publication No. 2006/0259098, entitled "SYSTEMS AND METHODS FOR USE IN PULSE GENERATION," which is incorporated herein by reference. Pulse generating circuitry 172 may comprise one or multiple pulse sources. Also, pulse generating circuitry 172 may operate according to constant voltage stimulation, constant current stimulation, or any other suitable mode of operation.

The various components of IMD 162 are powered by one or more internal batteries 170 (e.g., Li-ion rechargeable batteries). Battery 170 may be recharged by converting RF power radiated or received from external charger 102. Charging and communication circuitry 168 of IMD 162 is operative to couple to a coil 167 (referred to as a secondary coil) for effectuating near field coupling 150 with the coil 107 of external charger 102. When external charger 102 radiates RF power using its coil 107, the inductive coupling between the coil 107 of charger 102 with the coil 167 of IMD 162 causes an alternating current to be induced in the coil 167 of IMD 162. As will be set forth in detail further below, at least a portion of circuitry 168 may be configured to utilize the induced current in order to provide a charging voltage to battery 170 in a controllable manner. Also, in some embodiments, circuitry 168 may optionally use the same coil 167 to effectuate control communications signaling with charger 102. Further, it will be seen that an embodiment of the present disclosure advantageously uses only two feedthrough connections for connecting a coil-based frontend portion disposed in the header portion of IMD 162 to the rest of the internal circuitry of IMD 162. As skilled artisans will appreciate, the pulse generation circuitry 172 may be coupled to one or more stimulation leads through electrical connections provided in the header portion of the IMD's housing (i.e., feedthroughs), and by minimizing the number of feedthroughs used for connecting electrical conductors for other purposes (e.g., charging/communications), the number of leads that may be deployed in a stimulation therapy system may be advantageously maximized.

Figure 2:
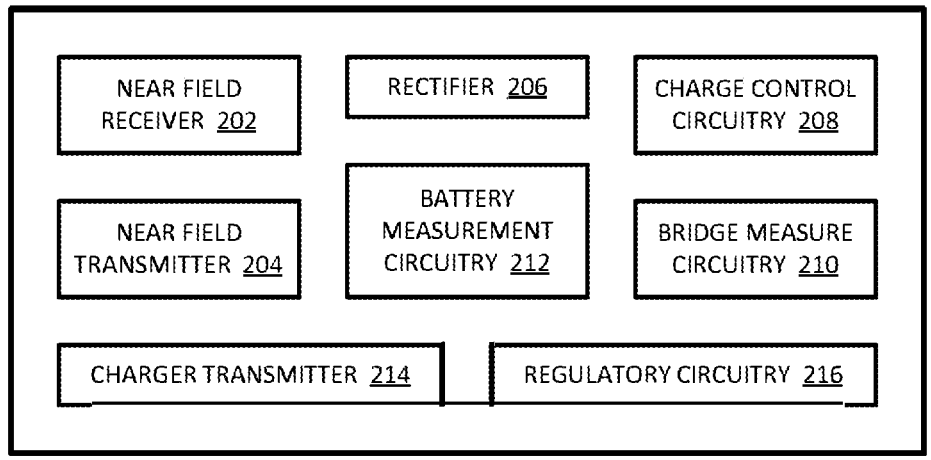
FIG. 2 depicts a block diagram illustrating additional details of charge control and communications circuitry of an example IMD according to an embodiment.

FIG. 2 depicts a block diagram of charging circuitry 200, which is a further representation of circuitry 168 of FIG. 1, illustrating additional components thereof according to one example embodiment. Circuitry 200 comprises coil and bridge rectifier circuitry 206, wherein a coil thereof (e.g., secondary coil 167 shown in FIG. 1) may be used for charging operations as well as communications with an external charger (e.g., charger 102) in some embodiments. In some other embodiments, the secondary coil may be used only for charging, with alterative links being available for communication purposes as previously noted. A near field receiver 202 is coupled to the coil, e.g., through a suitable capacitive arrangement as will be set forth further below. In one arrangement, receiver 202 may be configured to demodulate data when a carrier at an appropriate frequency is detected, whereupon a data stream may be communicated to controller 164. In similar fashion, near field transmitter 204 may be configured in one arrangement to receive a data stream from controller 164 for generating a modulated RF signal therefor, which may be applied to the secondary coil to communicate data via NFC to charger 102. Signal modulation and demodulation may, alternatively, be implemented in software executing on controller 164. Further, in some example embodiments, near field receiver 202 and transmitter 204 may be configured to not operate (e.g., disabled) when charging operations are taking place. Accordingly, a separate charger transmitter 214 may be employed to provide charging status messages to charger 102 when charging/discharging operations are being effectuated.

In one example arrangement, bridge measurement circuitry 210 may be provided to measure the output voltage of a bridge rectifier (described further below in reference to FIGS. 4 and 5) for control of charging operations. Regulatory circuitry 216 may be configured to control charging operations in response to one or more feedback/measurement signals (e.g., from bridge measurement circuitry 210). In one embodiment, when the output voltage is relatively low, regulatory circuitry 216 may be configured to allow circuitry 200 of the IMD to absorb RF power. Likewise, when the output voltage is relatively high, the coil may be clamped (e.g., shorted to ground) to prevent absorption of RF power in an example arrangement.

Charge control circuitry 208 may be provided to control the charging of battery 170. In one embodiment, charge control circuitry 208 may be configured to use the measurement functionality of battery measurement circuitry 212 to detect the state of battery 170. By way of illustration, battery measurement circuitry 208 may measure the battery voltage, charging current, battery discharge current, and/or the like. In some example embodiments, charge control circuitry 208 may prevent battery charging when an end-of-life (EOL) state has been reached for battery 154, which may be determined responsive to measurements provided by battery measurement circuitry 212. In further embodiments, charge control circuitry 208 may be configured to use a number of measurements to conduct fast charging operations as disclosed in greater detail in U.S. Patent Application Publication No. 2006/0259098, entitled "SYSTEMS AND METHODS FOR USE IN PULSE GENERATION," incorporated by reference hereinabove. In still further embodiments, charge control circuitry 208 may also be configured to monitor one or more output signals from bridge measurement circuitry 210 to further regulate the output voltage from bridge rectifier circuitry 206.

Figure 3:
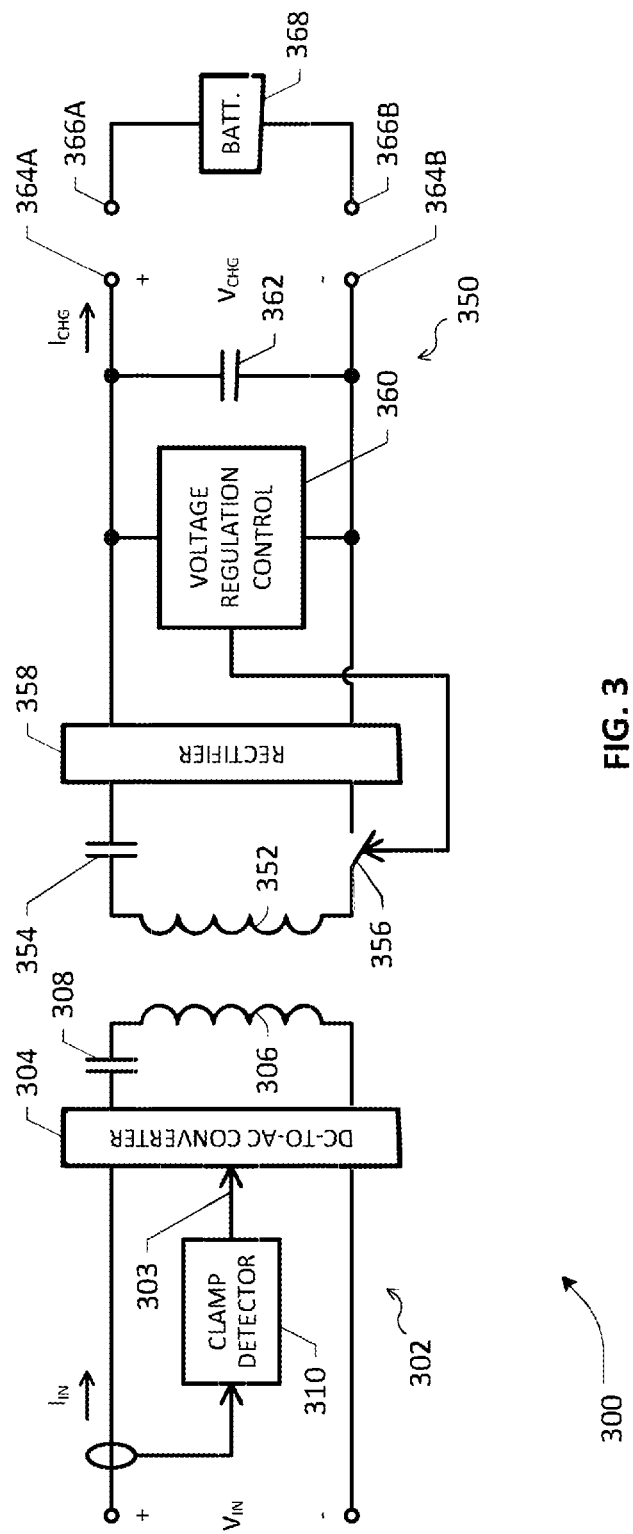
FIG. 3 is a block diagram of a wireless power transfer system for purposes of an example embodiment of the present invention.

FIG. 3 is a high level circuit block diagram of a wireless charging system 300 for purposes of an example embodiment of the present disclosure. Broadly, a power sender block 302 is operative as an external charger that supplies RF energy to a power receiver block 350 (e.g., an IMD) through respective series resonant coils that operate as a loosely coupled transformer (i.e., via magnetic coupling). A DC voltage input ($V_{IN}$) having a suitably configurable voltage range is provided to the power sender block 302, which includes a DC-to-AC converter 304 coupled to a sender-side tuning circuit comprising a primary coil 306 and a capacitor 308 connected in series. A clamp detector/monitor 310 may be included in the power sender block 302 for sensing the state of input current ($I_{IN}$). In one example embodiment, clamp detector/monitor 310 may be configured to generate a control signal 303 to DC-to-AC converter 304 in response to the input current status. It should be appreciated that DC-to-AC converter 304 is operative as a coil driver in order to supply adequate RF power to the power receiver block 350. When power receiver block 350 is not accepting power during a charging cycle (e.g., due to internal voltage/charging regulation and/or other internal ambient and status control signals), current flow through the sender-side tuning circuit is negligible (i.e., turned off), which condition may be sensed as a status change in the input current by the clamp detector/monitor circuitry 310 to generate control signal 303 operative to deactivate the power sender circuitry during the off state, thereby saving power.

To effectuate near field inductive RF power transfer, the power receiver block 350 is provided with a receiver-side tuning circuit comprising at least a secondary coil 352 coupled to at least a capacitor 354 in series (e.g., similar to the sender-side tuning circuit arrangement). An induced AC signal from the receiver-side tuning circuit is rectified by a rectifier 358, whose output may be optionally and/or suitably conditioned to apply power to a load, i.e., a battery 368 having terminals 366A, 366B. In an example arrangement, battery 368 may be disposed between output nodes 364A, 364B of conditioning circuitry having an output capacitor arrangement ($C_{OUT}$) 362 for providing a suitable DC output voltage ($V_{CHG}$ or $V_{OUT}$). In one example embodiment, voltage regulation control circuitry 360 may be coupled between the rectifier/conditioning portion 358 and battery load 368, which may be configured to generate one or more control signals for controlling a series switch arrangement 356 connected to the receiver-side tuning circuit arrangement, as will be set forth in further detail below.

It should be appreciated that the relationships between the sender-side coil voltage and current and the receiver-side coil voltage and current may be determined in an example implementation by the series tuning of the respective coils. For instance, such relationships may depend upon the operating frequency, tuning accuracy, coil separation, coil geometries, and the like. Accordingly, power transfer in an example arrangement involving wireless charging system 300 may in general depend on coupling between coils 306, 352, which in turn may depend on the distance between coils 306, 352, alignment, coil dimensions, coil materials, respective number of turns, magnetic shielding, impedance matching, applicable power band and associated resonant frequency, duty cycle, etc. Skilled artisans will recognize that at least some of these parameters may be selected in the design of an embodiment in order to comply with known or heretofore unknown wireless power transfer standards and specifications (e.g., Wireless Power Consortium WPC 1.1 Standard). Further, the voltage regulation control circuitry 360 may be appropriately configured in an example embodiment such that the time spent in the ON and OFF states may be suitably designed depending on the IMD application. In an example embodiment, accordingly, the time spent in the ON and OFF states may be determined based on an applicable voltage hysteresis band ($V_{HIGH}$–$V_{LOW}$), the rectifier output current $I_R$ and the load current $I_{OUT}$. In one example embodiment, an upper output threshold voltage $V_{HIGH}$ that begins clamping may be selected to be at 4.5V and a lower threshold voltage $V_{LOW}$ that ends clamping may be selected to be at 4.37 V, resulting in a nominal voltage hysteresis voltage of 0.13 V. In an example embodiment, the power sender block 302 may be configured to continually adjust its RF output power to maintain at least substantially constant power transfer to the power receiver block 350 across a range of distances. Further, certain additional design criteria may be implemented in order to achieve maximum power transfer efficiency in an implementation. For example, one requirement may be that the charger, i.e., power sender block 302, should deliver a select battery charging current suitable for a use case or application scenario. In an example use case, such a requirement may comprise a charging current of 50 mA. Another design requirement may be that the charger should deactivate during the OFF states to conserve power. Accordingly, in one arrangement, the clamp detector/monitor circuit 310 of the power sender block 302 may be configured to sense the time periods between clamping events of the power receiver block 350 in order to modulate the output power, as previously noted. Related details with respect to utilizing a clamp detection signal in a charging system may be found in U.S. Pat. No. 8,731,682, entitled "EXTERNAL CHARGING DEVICE FOR CHARGING AN IMPLANTABLE MEDICAL DEVICE AND METHODS OF REGULATING DUTY CYCLE OF AN EXTERNAL CHARGING DEVICE," incorporated by herein.

For purposes of the present invention, an example implementation of the wireless charging system 300 set forth above may be advantageously configured such that it involves only two feedthrough connections for connecting the receiver-side tuning circuit comprising coil 352 and capacitor 354 to the rest of the IPG internal circuitry. Moreover, the series switch arrangement 356 may be configured such that the receiver-side tuning circuit may be detuned or otherwise disabled during the OFF condition, thereby advantageously eliminating a high voltage condition that can develop during the time when the power receiver block 350 is in the clamped state because the receiver-side tuning circuit may be in resonance. As one skilled in the art will appreciate, the voltage in the secondary coil 352 can reach significantly high levels in the clamped state in some implementations (e.g., as high as 300V), which is highly undesirable in an IMD application.

Figure 4:
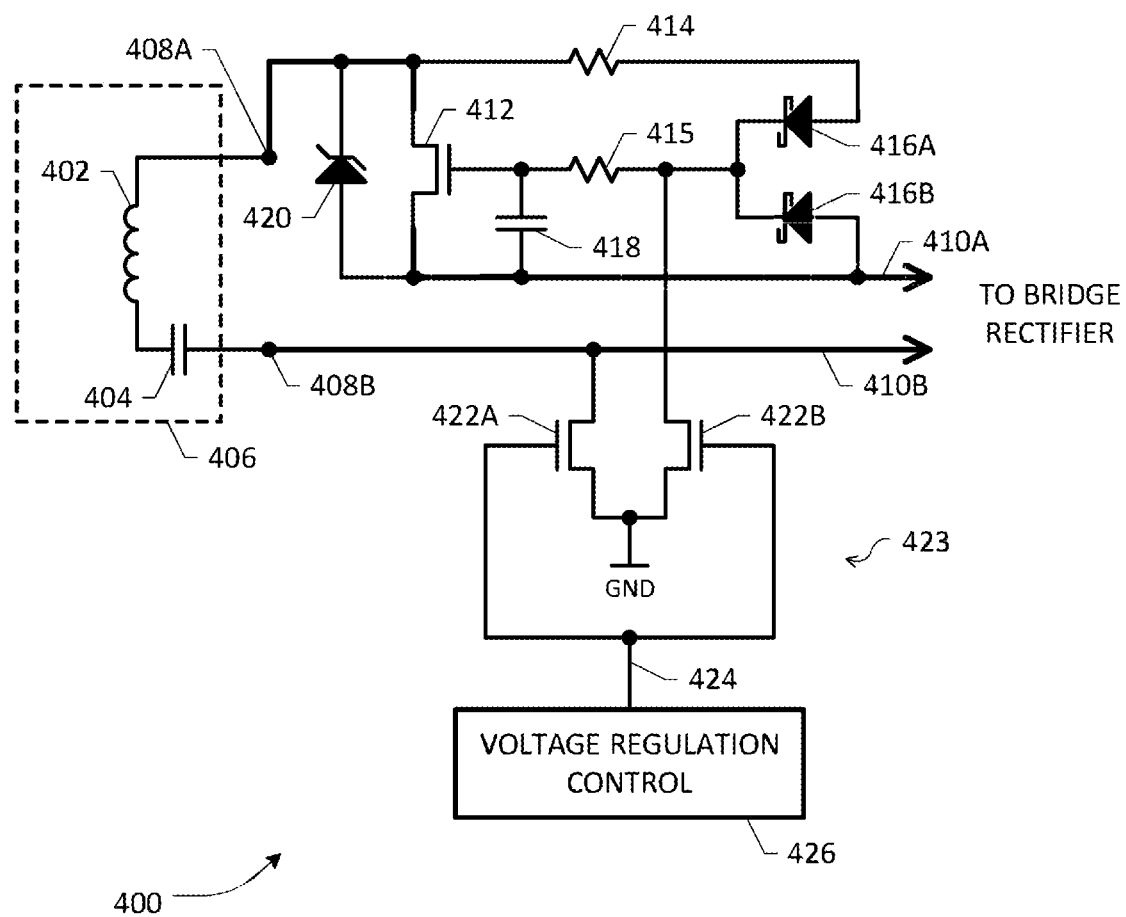
FIG. 4 is a circuit diagram of a frontend portion of a rechargeable IMD/IPG for facilitating wireless power transfer according to an embodiment of the present invention.

FIG. 4 depicts a circuit diagram of a frontend portion 400 of a rechargeable IMD/IPG device operating as a power receiver for facilitating wireless power transfer according to an example embodiment of the present disclosure. An inductive coupling element 406 comprising at least one inductor or coil 402 connected with at least one capacitor 404 in a series LC circuit configuration is operative as a receiver-side tuning circuit wherein the at least one capacitor 404 may be configured to be tunable over a range of frequencies. In one example implementation, coil 402 may comprise an inductor or its equivalent having an inductance of about 350-500 microhenries (μH) and tuning capacitor 404 may comprise a capacitance of about 500-1000 picofarads (pF) or its equivalent. Regardless of the actual number and/or type of inductors and/or tuning capacitors used in a particular implementation, a lumped-element model of the series LC circuit configuration of RF coupling element 406 may preferably be connected in an arrangement that defines a first electrical node 408A at a terminal of at least one inductor 402 and a second electrical node 408B at a terminal of at least one capacitor 404. Where the LC circuit configuration forming the inductive coupling element 406 is disposed in the IMD's header, nodes 408A/408B are operative to be electrically connected to the remainder of the frontend circuitry 400 via respective feedthroughs in accordance with the teachings herein. A series switch 412 is disposed between the first electrical node 408A and a trace 410A coupled to an input terminal of a bridge rectifier (not shown in this FIG.) for detuning the LC circuit element 406 during the OFF state of the power receiver. In one embodiment, switch 412 may comprise an N-channel metal oxide semiconductor field-effect transistor (NMOS FET) that may be opened when the charging is OFF. During the ON period, switch 412 may be configured to be automatically closed by deriving a gate drive voltage from the LC circuit element 406. On the other hand, switch 412 may be configured to be opened in the OFF state responsive to a gate control signal derived from a clamp signal using appropriate logic circuitry. Skilled artisans will recognize upon reference hereto that suitable switch protection circuitry and/or ON-state gate control circuitry may provided using appropriate electrical/electronic components including but not limited to, inter alia, capacitors, transistors, FETs, diodes, etc., in various combinations to control and condition power transfer operations depending on a particular wireless power transfer application.

In one implementation, a Zener diode 420 may be connected between drain and source nodes/terminals of switch 412 in order to provide protection therefor against inductive spikes. For example, a Zener diode of appropriate electrical characteristics may be disposed for providing clamping protection against inductive spikes at around 30 V to 60 V. A pair of Schottky diodes 416A, 416B coupled in a configuration such that respective cathodes thereof are commonly connected to a resistor 415, which in turn is connected to a gate of switch FET 412. A capacitor 418 may be disposed between the gate and one of the terminals of switch FET 412 (e.g., source node coupled to bridge rectifier trace 410A). Anode terminal of Schottky diode 416A is coupled to a resistor 414, which in turn is commonly connected to the cathode terminal of Zener diode 420, first electrical node 408A and a terminal of switch FET 412 (e.g., drain). On the other hand, anode terminal of Schottky diode 416B may be directly coupled to bridge rectifier trace 410A. In one implementation, resistor 414 may have a resistance of about 5-15 kΩ and resistor 415 may have a resistance of about 0.5-1.5 kΩ. In one implementation, capacitor 418 may comprise a capacitor rated to about 50 V ±10% and having a capacitance of about 500-1500 pF.

Figure 5:
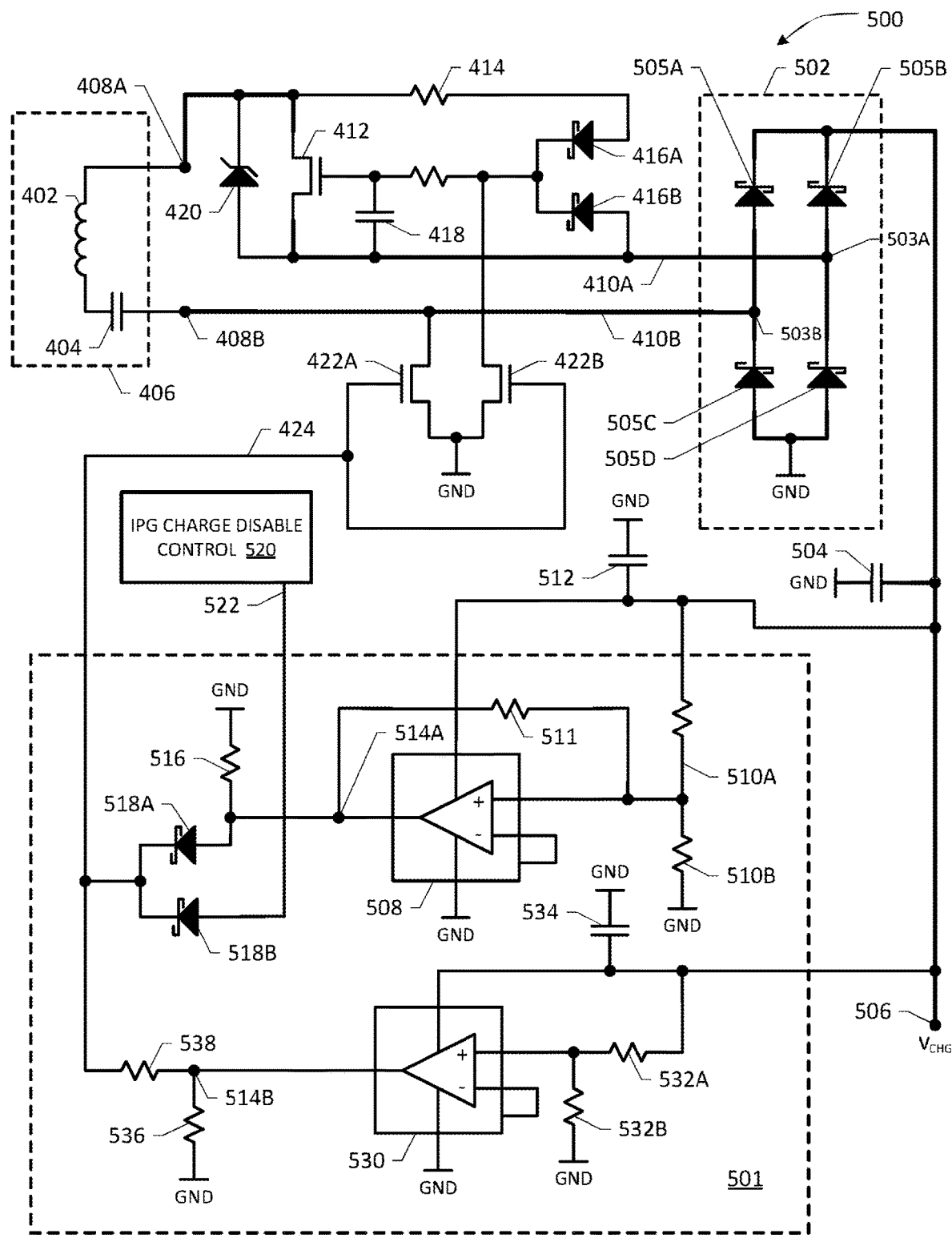
FIG. 5 depicts a circuit portion including voltage regulation circuitry that may be practiced in association with the frontend portion of FIG. 4 for purposes of an example embodiment of the present invention.

Appropriate control signaling for the LC circuit configuration of inductive coupling element 406 and as well as gate control for switch 412 may be effectuated by way of a frontend control signaling portion 423 (referred to herein as a "clamp circuit" or "clamp control circuitry") that is driven by a clamp control signal 424 generated by a voltage regulation control block 426 operative to provide clamping as well as optional over-voltage protection in one embodiment, which will be described in further detail below in reference to FIG. 5. In one implementation, clamp control signaling portion 423 comprises a pair of FETs 422A/422B whose respective gates are driven by clamp control signal 424, wherein source terminals thereof are commonly tied to a reference potential, e.g., ground. Whereas a drain terminal of FET 422B is connected to the common cathode connection of Schottky diodes 416A, 416B, a drain terminal of FET 422A is connected the second electrical node 408B formed at a terminal of at least one capacitor 404 of the LC circuit configuration. Further, the second electrical node 408B is also coupled to a trace 410B extending to a second input terminal of the bridge rectifier (shown in FIG. 5). In one implementation, when clamp control signal 424 is asserted (e.g., a logic high) during the OFF state, gate voltages of FETs 422A and 422B are driven high, thereby causing FETs 422A and 422B to be turned on. As FET 422A is turned on, the second electrical node 408B connected to bridge rectifier trace 410B is pulled to ground. At the same time, as FET 422B is turned on, it causes the gate terminal of series switch FET 412 to be pulled to ground. Accordingly, series switch FET 412 is turned off, thereby opening the series connection path between the first electrical node 408A and bridge rectifier trace 410A. As a result, the series LC circuit is opened during the OFF state, whereby it is caused to be detuned with respect to a primary coil in the external charger. Since it is detuned, there is no resonance-caused high voltage condition developed in the receiver-side circuitry of an IMD. As noted above, series switch FET 412 is automatically closed in the ON state (e.g., clamp control signal 424 is deasserted), wherein a suitable gate drive voltage is derived from the LC circuit component 406 whose output is conditioned through the Schottky diode arrangement 416A/416B.

FIG. 5 depicts a circuit portion 500 including voltage regulation circuitry 501 that may be practiced in association with a bridge rectifier (BR) arrangement 502 as well as the frontend portion 400 of FIG. 4 for purposes of an example embodiment of the present invention. Traces 410A and 410B carrying induced AC signals from the frontend circuitry 400 are coupled to two corresponding input nodes/terminals 503A and 503B of the BR circuit arrangement 502 that is operative to output a charging voltage VCHG at an output node 506, which may be coupled to an IMD's battery, e.g., a Li-ion battery. In one example embodiment, BR circuit 502 may comprise a full-wave rectifier having four diodes 505A-505D, with diodes 505A and 505B having a common output to node 506 and diodes 505C and 505D having a common ground. An example implementation of BR circuit 502 may include four Schottky diodes having low forward bias voltages and faster switching capabilities. Skilled artisans will recognize that in alternative and/or additional embodiments a BR circuit implementation may involve various other electronic devices or components such as, e.g., FETs, silicon-controlled rectifiers (SCRs) or thyristors, etc., without limitation. Similar to the circuit arrangement shown in FIG. 3, a suitable output capacitor 504 (e.g., having a capacitance of about 50 μF to 250 μF rated at around 10.0 V ±10%) may be disposed between output node 506 and ground for conditioning the charging voltage supplied to the battery.

In accordance with the teachings herein, an embodiment of the present invention includes suitable voltage regulation circuitry 501 operative to provide clamp control signaling, e.g., control signal 424, that may be advantageously implemented so as to achieve the objective of powering the circuitry from RF power rather than the battery (i.e., "zero-volt" operation). Preferably, the voltage regulation circuitry 501 may be configured such that certain output nodes are maintained in a known state as the IPG/IMD's charging voltage ramps up from 0 V. Since the areas of concern during the ramp-up stage are the states of any logic circuit components used in the regulation circuitry (e.g., op amps, comparators, etc.) for detecting the $V_{CHG}$ levels (which in turn is used in generating clamp control signaling), an example arrangement herein facilitates known voltage states to be provided in association with the logic circuit components rather than having indeterminate or floating output nodes coupled to the clamp control signal path 424. In one arrangement where a two-tier or two-level voltage comparison is utilized for regulation (e.g., one comparison for detecting a target $V_{CHG}$ level and another comparison at a higher voltage as a backup regulation or protection), two separate comparators having respective reference voltages may be provided for detection and subsequent activation of the clamping circuitry (e.g., circuitry 423 shown in FIG. 4). Accordingly, in such an implementation, two comparators 508, 530 may be provided to activate the clamping circuitry: a first comparator 508 that operates at the target $V_{CHG}$ voltage to provide a detuning signal; and a second comparator 530 that operates at a slightly higher voltage providing over-voltage protection if the target charge comparator, i.e., first comparator 508 fails. Ideally the output of comparators 508, 530 should remain low until $V_{CHG}$ exceeds the target voltage. While low-voltage comparators that operate down to 1.7 V may be used in an example implementation, there is still uncertainty in their output states until the respective minimum operating voltages are reached. Since the outputs of comparators 508, 530 are utilized in driving the gates of low-threshold FETs 422A/422B of the clamping circuitry portion 423 (e.g., FETs having a minimum 0.65 V gate threshold), the outputs of comparators 508, 530 must remain below this gate threshold while their respective supply voltages (derived from the rectified output of BR circuitry 502) ramp up. In an example implementation, respective comparators' output vs. supply voltages may be suitably characterized in order to determine a corresponding output resistive loading needed to maintain the output voltage at a known value. In a test case scenario, for example, the comparators' outputs may be weak (e.g., unable to deliver more than 2 µA) prior to reaching operating voltage. In such a scenario, an output 514A of first comparator 508 (which may also be referred to as a voltage clamp comparator) may be loaded with a grounded loading resistor 516 (e.g., 10 kΩ to 40 kΩ) operative to limit the comparator's output to a particular voltage level (e.g., 60 mV) that is less than the gate threshold voltage of FETs 422A/422B so as to ensure that they are not switched on during the ramp-up stage. Likewise, an output 514B of second comparator 530 (also referred to as an over-voltage shutoff comparator) may be loaded with a grounded loading resistor 536 (e.g., 10 kΩ to 40 kΩ) which may be disposed in series with another resistor 538 (e.g., 10 kΩ to 40 kΩ) in a voltage divider arrangement to further reduce the output voltage to a specified value.

Skilled artisans will recognize upon reference hereto that the foregoing voltage regulation circuitry 501 may be implemented in different ways depending on the requirements of a particular IMD and/or battery charging application. Without limitation, some of the implementational aspects of an embodiment are set forth as follows. For example, the functionality of comparator 508 may be realized by way of a differential op amp circuit having a single-ended output, wherein one of the inputs is internally connected to a reference (e.g., at around 1.25 V) whereas the other input is coupled to a voltage level derived from the $V_{CHG}$ level via a voltage divider comprising resistors 510A and 510B. In one implementation, resistor 510A may have a resistance of about 25 kΩ to 30 kΩ) and resistor 510B may have a resistance of about 5.0 kΩ to 15 kΩ). A first supply voltage ($V_S$) is derived from the $V_{CHG}$ level that is conditioned via a grounded capacitor 512 (e.g., having a capacitance of about 0.1 µF rated at around 16.0 V±10%), with a second supply terminal connected to ground. A feedback resistor 511 having a resistance of about 0.5 MΩ to 1.5 MΩ may be coupled between output 514A and one of the inputs of comparator 508. A charge disable control circuit 520 may optionally be provided as part of an IMD implementation wherein a control signal 522 may be generated in order to disable unintended and/or undesirable charging operations due to, e.g., the presence of external stimuli such as imaging/scanning equipment (for instance magnetic resonance imaging or MRI), detection of high temperatures associated with the battery and/or IMD, etc. In one implementation, the output signal of comparator 508 may be logically OR'ed with charge disable control signal 522 to generate a control signal operative as the clamp control signal 424 which may be pulled high when either the output 514A or charge disable control signal 522 is high. In one example embodiment, a pair of Schottky diodes 518A and 518B respectively driven by comparator output 514A and charge disable control signal 522 but having a common output may be provided for implementation of such logic.

In a further example, over-voltage shutoff comparison functionality of the voltage regulation circuitry 501 may be optionally provided as an additional protection scheme that comes into operation when the voltage clamp comparison functionality fails. As noted above, comparator 530 may be implemented in such a scenario to support the over-voltage shutoff comparison functionality. Similar to the implementation of comparator 508, the functionality of comparator 530 may also be realized by way of a differential op amp circuit having a single-ended output, wherein one of the inputs is internally connected to a reference (e.g., at around 0.2 V) whereas the other input is coupled to a voltage level derived from the $V_{CHG}$ level via a corresponding voltage divider comprising resistors 532A and 532B. In one implementation, resistor 532A may have a resistance of about 25 kΩ to 45 kΩ) and resistor 532B may have a resistance of about 0.5 kΩ to 2.5 kΩ). A supply voltage ($V_S$) is derived from the $V_{CHG}$ level that is conditioned via a grounded capacitor 534 (e.g., having a capacitance of about 0.1 µF rated at around 16.0 V), with a second supply terminal connected to ground. An over-voltage shutoff signal provided at node 514B is conditioned to operate as clamp control signal 424 via the resistor arrangement 536/538 as noted above. In one implementation, first comparator 508 may be appropriately biased such that a detune signal may be generated at 4.45 V, with a hysteresis of about 122 mV. In similar fashion, second comparator 530 may be arranged with appropriate biasing such that an over-voltage shutoff signal may be generated at 4.84 V, with a hysteresis of about 0.9 mV.

Figure 6:
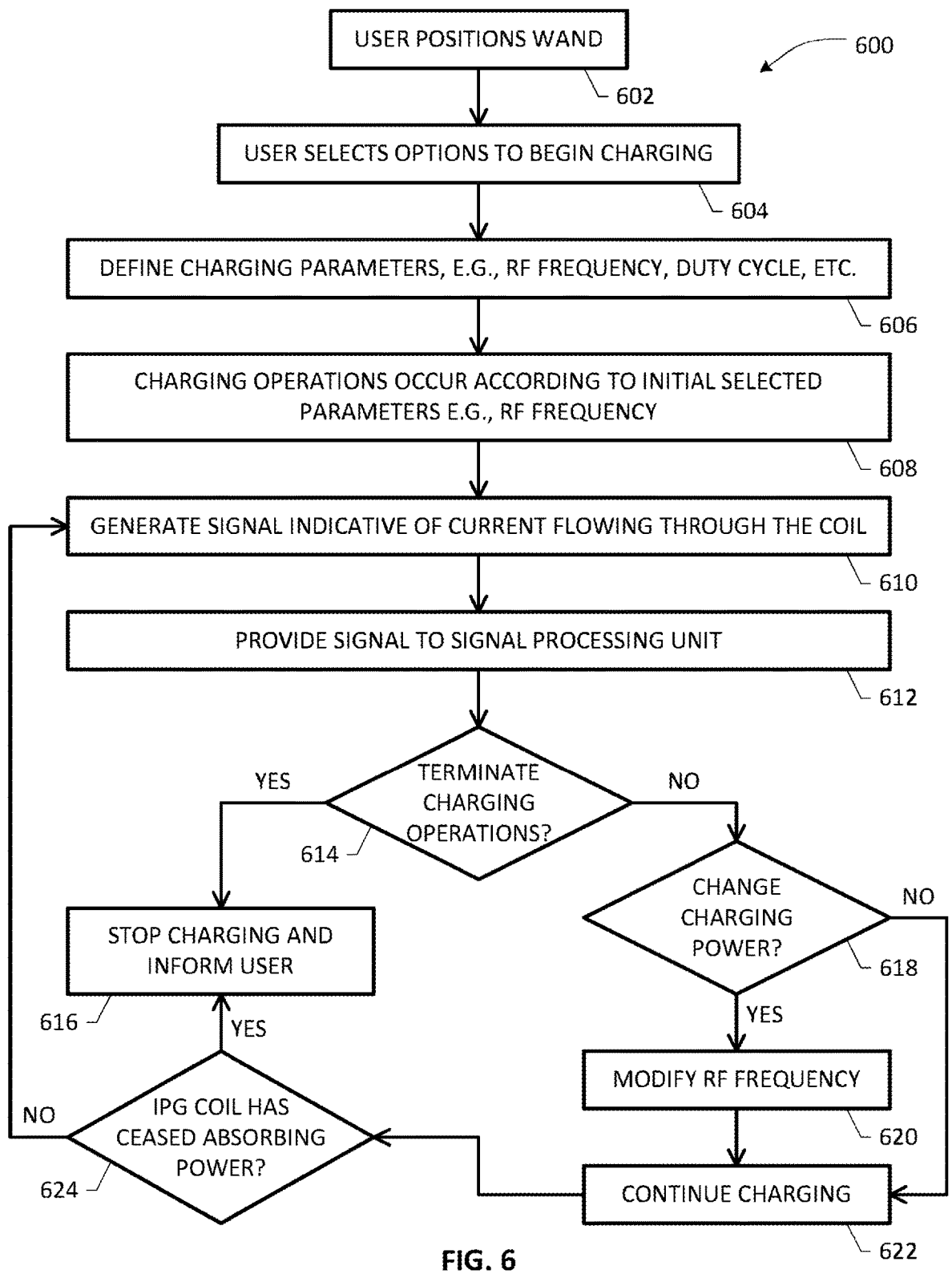
FIG. 6 depicts a flowchart of blocks, steps and/or acts that may be (re)combined in one or more arrangements with or without additional flowcharts of the present disclosure for facilitating charging operations according to some embodiments of the present disclosure.

FIG. 6 depicts a flowchart of blocks, steps and/or acts that may be (re)combined in one or more arrangements with or without additional flowcharts of the present disclosure for facilitating IMD charging operations according to some embodiments of the present disclosure. By way of illustration, example process 600 may commence at block 602 where a user positions a charging wand/device adjacent to the patient's body at a location near to the implant site of an IMD to effectuate communications and/or charging. At block 604, the user selects an option on the external charging device to begin charging operations. At block 606, appropriate charging parameters may be defined, selected and/or configured. For example, RF parameters, initial duty cycle information, etc. may be selected or defined for charging. At block 608, charging operations may occur by driving the coil of the charging wand at a suitable RF frequency according to the selected duty cycle. At block 610, a signal indicative of the current flowing through the coil may be generated. At block 612, the flow indication signal may be provided to a demodulation circuit to detect charging status messages communicated from the implanted medical device. Alternatively, the signal may be sampled and processed by a suitable signal processing routine to demodulate the charging status messages. In an example arrangement, the signal may be sampled using an on-chip analog-to-digital converter (ADC) of the microcontroller of the external charging device.

At block 614, a determination or logical comparison may be made to determine whether a status message indicates the charging operations should be terminated. If so, charging stops and one or more suitable notification messages may be provided to the user as set forth at block 616. In an example arrangement, the notification message(s) may indicate to the user that the battery of the implantable medical device is fully charged, the battery has reached an end-of-life (EOL) state and should be replaced, or some error or malfunction has taken place, and the like. If the logical comparison indicates that charging should continue, the process flow continues to decision block 618, where a further determination or logical comparison may be made in order to determine whether charging power should be changed, e.g., if additional power is appropriate or acceptable to the IMD. If so, the process flow proceeds to block 620 where the duty cycle and/or RF parametric information may be modified to drive the coil accordingly. Whether or not the charging parameters have been changed, the process flow continues with charging operations according to the updated or previous settings, as set forth at block 622. At block 624, a determination may be made to identify whether the coil of the implantable medical device has ceased absorbing RF power. If so, the process flow continues to block 616 whereby the charging operation ceases and appropriate user messages may be generated. In one example implementation, the process flow may return to block 610 to continue monitoring the control signals indicative of current flow through the coil so as to modulate the charging operations accordingly. In some implementations, the transmitter-side coils and capacitance may be specified and the resonant frequency point may be fixed accordingly. For example, power transfer may be regulated by changing the frequency along a suitable resonance curve depending on the use case or application scenario, e.g., from 112 kHz to 205 kHz or from 260 kHz to 300 kHz, where higher the frequency is on the resonance curve, the lower the power that is transmitted.

Skilled artisans will recognize that appropriate portions of the flowchart of FIG. 6 may be implemented in some embodiments using software instructions or code executing on a controller or processor of the external charging device and/or the IMD to control the various hardware circuits respectively thereof. It will be further appreciated that in a rearrangement of the foregoing blocks, acts, and functions of the flowchart of FIG. 6, an embodiment may be implemented using the wireless power transfer circuitry of the present invention for effectuating a method of charging an IMD/IPG implanted within a patient for providing stimulation therapy, wherein the method comprises: positioning an external charger proximate to the patient for effectuating a near field coupling relationship with the IMD, wherein the external charger includes a primary coil and the IMD includes a secondary coil; selecting one or more charging parameters for driving the primary coil to generate RF power at a particular frequency, the RF power inducing a voltage in the secondary coil of the IMD; converting the induced voltage to a charging voltage by a bridge rectifier of the IMD; and detecting clamping of the secondary coil due to at least one of: (i) detuning the secondary coil caused by opening a series switch disposed between the bridge rectifier and the secondary coil, and (ii) assertion of a voltage clamp control signal generated responsive to monitoring a target voltage level of the charging voltage generated by the bridge rectifier. As noted above with respect to FIG. 5, an overvoltage level with respect to the target voltage may also be monitored for generating a clamp control signal in an optional implementation. The external charger may be configured to monitor, detect, or otherwise sense a rate of occurrence of clamping at the secondary coil; and responsive to the monitoring of the rate of occurrence of clamping, the frequency of RF power generated by the primary coil may be modified. In one embodiment, the foregoing method may involve monitoring the rate of occurrence of clamping over a defined period of time, which may be configurable or otherwise variable based on the IMD application and/or the status of battery charging. In one embodiment, the frequency of the RF charger may be increased to lower the RF power responsive to determining that the rate of occurrence of clamping over the defined period of time is greater than a predetermined threshold. In one embodiment, the frequency of the RF charger may be reduced to increase the RF power responsive to determining that the rate of occurrence of clamping over the defined period of time is less than a predetermined threshold.

Figure 7:
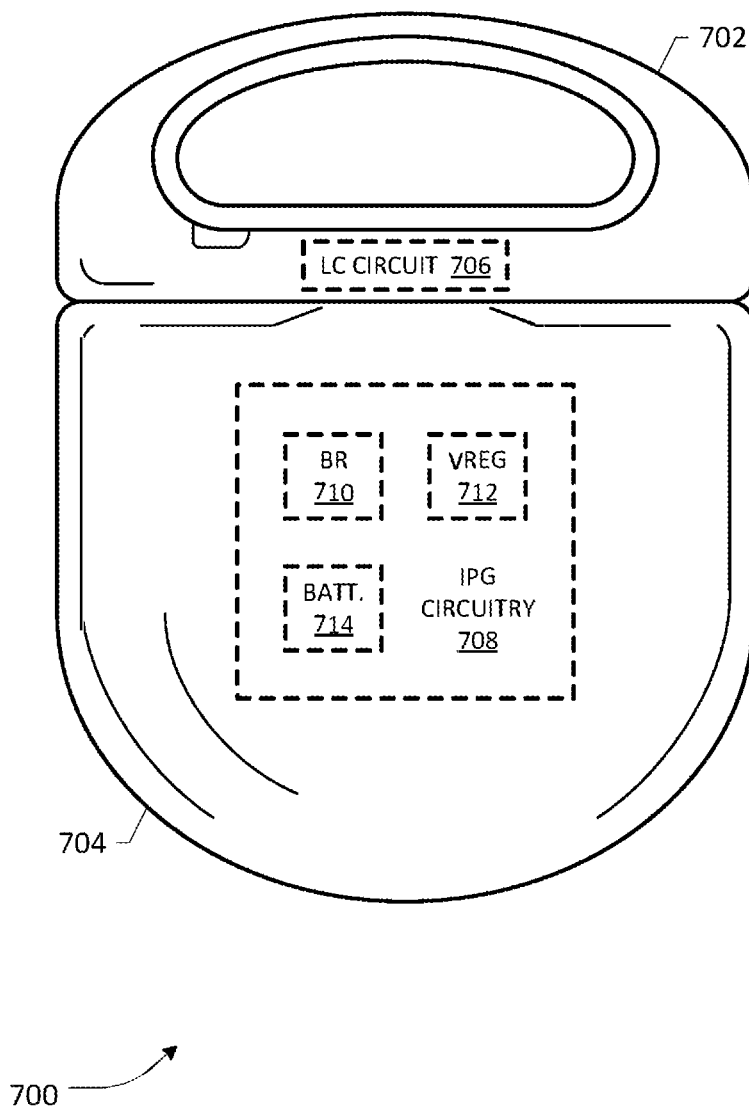
FIG. 7 depicts an example IMD/IPG having a header portion and a body portion wherein an embodiment of the present invention may be practiced.

FIG. 7 depicts an example IMD/IPG housing 700 having a header portion 702 and a body portion 704 wherein an embodiment of the present invention may be practiced. Regardless of any particular form factor, header portion 702 may preferably be configured to operate as a housing portion for an inductive coupling component or circuit that may comprise one or more inductors and one or more tuning capacitors in a series LC configuration 706 having two feedthrough terminals. Likewise, body portion 704 may be configured to house an IPG circuit portion 708 that may include various pieces of the circuitry described in detail hereinabove, e.g., including frontend circuitry portion, bridge circuitry portion, voltage regulation circuitry portion, battery, etc., as exemplified by various blocks 710, 712, 714, in addition to one or more other blocks or functionalities set forth in reference to FIG. 9. As previously noted, electrical connectivity between LC configuration circuit 706 and IPG circuit portion 708 may be accomplished using only two feedthrough paths controlled by a series detuning switch in accordance with the described above, whereby the availability of remaining feedthroughs may be maximized for other purposes (e.g., for supporting additional lead systems).

Figure 8A:
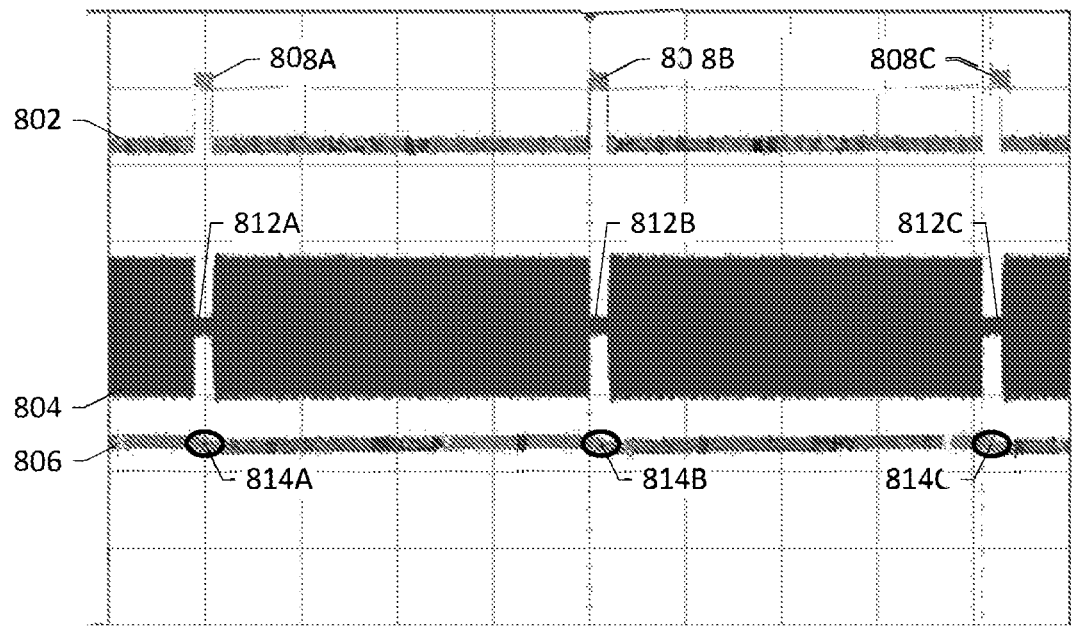
FIGS. 8A and 8B depict example waveforms associated with one or more signals generated and/or monitored during the operation of a wireless power transfer circuit according to an example embodiment of the present invention.
Figure 8B:
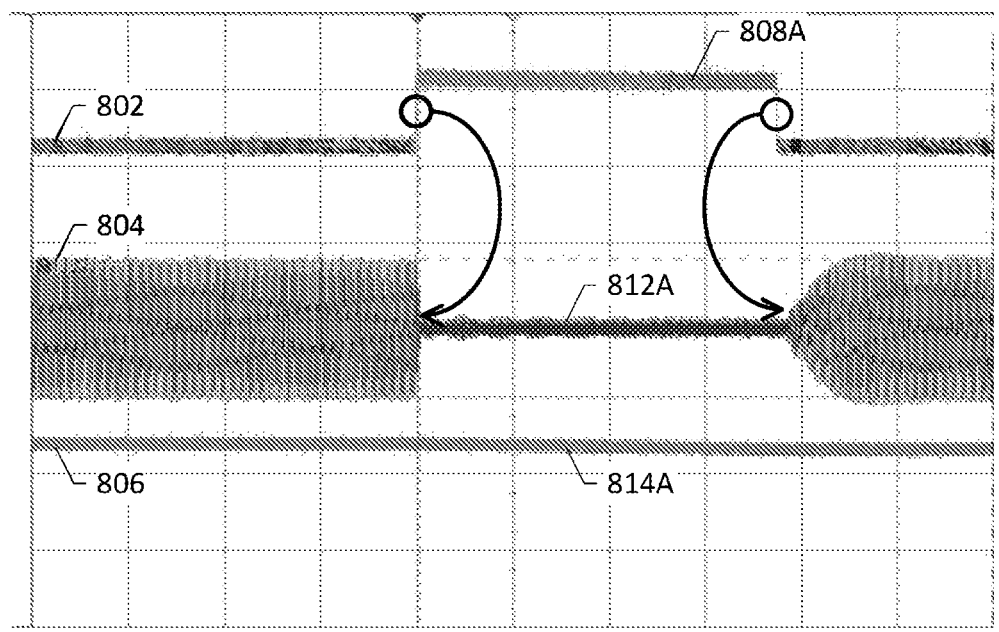

FIGS. 8A and 8B depict example waveforms associated with one or more signals generated and/or monitored during the operation of a wireless power transfer circuit according to an example embodiment of the present invention. In particular, FIG. 8A illustrates a panel 800A that exemplifies a waveform set corresponding to multiple cycles of a clamp control signal 802 (e.g., corresponding to three assertions), whereas FIG. 8B illustrates a panel 800B that exemplifies a magnified portion associated with a single assertion of the clamp control signal 802. As illustrated, clamp control signal 802 is shown with three assertions 808A-808C in panel 800A, each of which causing a corresponding reduction in a coil current 804, illustrated by notches 812A-812C. Reduction in the IPG coil current 804 and/or the clamp control signaling may be sensed/monitored by circuitry in the charging device via suitable telemetry (in-band or out-of-band) for adjusting the RF parameters as needed. Corresponding to the reduction in the IPG coil current, charging voltage ($V_{CHG}$) 806 undergoes a reduction as illustrated by slopes 814A-814C. Since the clamping operation (i.e., an assertion or logic high level in the clamp control signal 802) effectively reduces coil current and causes output voltage to fall as the output capacitor discharges, the falling slope of the output voltage may be dependent on the output stage's RC time constant. When the clamp control signal 802 is on OFF state, i.e., it is deasserted or in logic low state), the coil current 804 flows again, which may rise according to a corresponding rise time. Panel 800B of FIG. 8B illustrates the effects of the assertion 808A in clamp control signal 802 and its subsequent deassertion on the coil current 804 and corresponding fall and rise of the output voltage 806 in an example implementation.

In general, the frequency of the ON/OFF cycles in charging operations is given by: $f=[1/(T_{OFF}+T_{ON})]$, with $T_{OFF}$ and $T_{ON}$ respectively defining the time spent in the OFF and ON states, which in turn are dependent on the required hysteresis range of the charging voltage $V_{CHG}$, output capacitance, rectifier current ($I_R$) and load or output current ($I_{OUT}$). During the OFF time, the output current is approximately equal to the battery charging current. In one particular implementation having a nominal hysteresis voltage of 0.13 V (e.g., resulting from a $V_{HIGH}$ of 4.50 V and a $V_{LOW}$ of 4.37 V) and a given battery charging current of 50 mA and output capacitance of 141 μF, $T_{OFF}$ may be determined as $[(V_{HIGH}-V_{LOW}) \times C_{OUT}]/I_{OUT}$, which works out to be 367 μs. As described above, the external charger senses the OFF time clamping action and accordingly adjusts its output so that the clamping frequency is between 100 Hz and 200 Hz (i.e., clamping once every 5 ms to 10 ms) in the foregoing example implementation.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Skilled artisans will recognize upon reference hereto that various switching components of one or more circuits described herein may be implemented using a variety of monolithic or integrated semiconductor devices known in the electrical arts, e.g., including but not limited to bipolar junction transistors (BJTs), metal oxide semiconductor field effect transistors (MOSFETS), junction gate FETs (JFETs), n-channel MOSFET (NMOS) devices, p-channel MOSFET (PMOS) devices, depletion-mode or enhancement-mode devices, and the like, as well as any logic gates built therefrom. Likewise, various types of comparators, e.g., inverting and/or non-inverting comparators, latched comparators, single ended comparators, differential op amp circuits and the like may be implemented in an example embodiment. It will be further understood that the sizing (e.g., channel width and length) and biasing of the switching devices used in any of the components can be highly configurable, depending on the voltage/current ratings, application requirements, and the like.

Further, in at least some additional and/or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. An implantable medical device (IMD) configured to provide stimulation therapy to a patient, the IMD comprising:
   a rechargeable battery;
   pulse generating circuitry powered by the rechargeable battery;
   an inductive coupling element including at least one inductor (L) and at least one capacitor (C) coupled to the at least one inductor in a series LC circuit configuration operative to accept radio frequency (RF) power from an external charger, the series LC circuit configuration defining a first electrical node at a terminal of the at the least one inductor and a second electrical node at a terminal of the at least one capacitor;
   a bridge rectifier operative to generate a charging voltage at an output node of the bridge rectifier from an induced voltage provided by the inductive coupling element when magnetically coupled to the external charger to receive the RF power;
   a series switch disposed between the first electrical node of the series LC circuit configuration and the bridge rectifier;
   voltage regulation circuitry operative to regulate a level of the charging voltage generated at the output node of the bridge rectifier for charging the rechargeable battery; and
   a coil clamp circuit configured to change the series switch to an OFF state based on an output of the voltage regulation circuitry to detune the inductive coupling element, whereby a high voltage condition is prevented from developing in the series LC circuit configuration of the inductive coupling element.

2. The IMD as recited in claim 1, wherein the series switch comprises an N-channel metal oxide semiconductor (NMOS) field-effect transistor (FET) device driven by a gate voltage derived from the series LC circuit configuration in an ON state.

3. The IMD as recited in claim 2, wherein the NMOS device is opened in the OFF state by clamping the gate voltage to a ground using a first FET device of the coil clamp circuit that is driven by a clamp control signal generated by the voltage regulation circuitry.

4. The IMD as recited in claim 3, wherein the coil clamp circuit comprises a second FET device disposed in a parallel circuit configuration with the first FET device, the second FET device coupled to the second electrical node of the series LC circuit configuration and driven by the clamp control signal generated by the voltage regulation circuitry.

5. The IMD as recited in claim 1, wherein the voltage regulation circuitry comprises a first comparator configured to compare a target voltage level of the charging voltage generated by the bridge rectifier with an internal reference voltage associated with the first comparator.

6. The IMD as recited in claim 5, wherein an output of the first comparator is coupled to a grounded loading resistor for preventing asserting a logic high value of the clamp control signal until an operating voltage of the first comparator comprising the target voltage level is reached.

7. The IMD as recited in claim 5, wherein the voltage regulation circuitry comprises a second comparator configured to compare an over-voltage shutoff level that is greater than the target voltage level by a select amount with an internal reference voltage associated with the second comparator.

8. The IMD as recited in claim 7, wherein an output of the second comparator is coupled to a grounded loading resistor for preventing asserting a logic high value of the clamp control signal until an operating voltage of the second comparator comprising the over-voltage shutoff level is reached.

9. The IMD as recited in claim 1, wherein the inductive coupling element is open when the series switch is in the OFF state.

10. The IMD as recited in claim 1, wherein the inductive coupling element is not connected to ground when the series switch is in the OFF state.

11. A stimulation system, comprising:
    an implantable medical device (IMD) implanted within a patient to provide stimulation therapy to a specific tissue of the patient, the IMD comprising a rechargeable battery and pulse generating circuitry powered by the rechargeable battery; and
    an external charger including a primary coil configured to effectuate a near field coupling relationship with the IMD when positioned proximate to a region of the patient having the IMD,
    wherein the IMD includes:
      an inductive coupling element comprising at least one inductor (L) and at least one capacitor (C) coupled to the at least one inductor in a series LC circuit configuration operative to accept radio frequency (RF) power from the external charger, the series LC circuit configuration defining a first electrical node at a terminal of the at least one inductor and a second electrical node at a terminal of the at least one capacitor;
      a bridge rectifier operative to generate a charging voltage at an output node of the bridge rectifier from an induced voltage provided by the inductive coupling element when magnetically coupled to the external charger to receive the RF power;
      a series switch disposed between the first electrical node of the series LC circuit configuration and the bridge rectifier;
      voltage regulation circuitry operative to regulate a level of the charging voltage generated at the output node of the bridge rectifier for charging the rechargeable battery; and a coil clamp circuit configured to change the series switch to an OFF state based on an output of the voltage regulation circuitry to detune the inductive coupling element, whereby a high voltage condition is prevented from developing in the series LC circuit configuration of the inductive coupling element.

12. The stimulation system as recited in claim 11, wherein the inductive coupling element is disposed in a header portion so that only two feedthroughs are utilized in connecting the inductive coupling element to a first input node of the bridge rectifier via the series switch and to a second input node of the bridge rectifier, and further wherein the series switch, the bridge rectifier, the voltage regulation circuitry and the coil clamp circuit are disposed in a device housing of the IMD to which the header portion is hermetically coupled.

13. The stimulation system as recited in claim 12, wherein the external charger comprises:
a clamp detector configured to detect clamping of the series LC circuit configuration due to at least one of: (i) detuning the series LC circuit configuration caused by opening the series switch, and (ii) assertion of a voltage control signal generated responsive to monitoring a target voltage level of the charging voltage generated by the bridge rectifier; and
a controller for monitoring a rate of occurrence of clamping at the series LC circuit configuration and, responsive to the monitoring of the rate of occurrence of clamping, for modifying a frequency of the RF power generated by the primary coil.

14. The stimulation system as recited in claim 13, wherein the series switch comprises an N-channel metal oxide semiconductor (NMOS) field-effect transistor (FET) device driven by a gate voltage derived from the series LC circuit configuration in an ON state.

15. The stimulation system as recited in claim 14, wherein the NMOS device is opened in the OFF state by clamping the gate voltage to a ground using a first FET device of the coil clamp circuit that is driven by a clamp control signal generated by the voltage regulation circuitry.

16. The stimulation system as recited in claim 15, wherein the coil clamp circuit comprises a second FET device disposed in a parallel circuit configuration with the first FET device, the second FET device coupled to the second electrical node of the series LC circuit configuration and driven by the clamp control signal generated by the voltage regulation circuitry.

17. The stimulation system as recited in claim 13, wherein the voltage regulation circuitry comprises a first comparator configured to compare a target voltage level of the charging voltage generated by the bridge rectifier with an internal reference voltage associated with the first comparator.

18. The stimulation system as recited in claim 17, wherein an output of the first comparator is coupled to a grounded loading resistor for preventing asserting a logic high value of the clamp control signal until an operating voltage of the first comparator comprising the target voltage level is reached.

19. The stimulation system as recited in claim 17, wherein the voltage regulation circuitry comprises a second comparator configured to compare an over-voltage shutoff level that is greater than the target voltage level by a select amount with an internal reference voltage associated with the second comparator.

20. The stimulation system as recited in claim 19, wherein an output of the second comparator is coupled to a grounded loading resistor for preventing asserting a logic high value of the clamp control signal until an operating voltage of the second comparator comprising the over-voltage shutoff level is reached.

21. A stimulation system, comprising:
an implantable medical device (IMD) implanted within a patient to provide stimulation therapy to a specific tissue of the patient, the IMD comprising a rechargeable battery and pulse generating circuitry powered by the rechargeable battery; and
an external charger including a primary coil configured to effectuate a near field coupling relationship with the IMD when positioned proximate to a region of the patient having the IMD,
wherein the IMD includes:
an inductive coupling element comprising at least one inductor (L) and at least one capacitor (C) coupled to the at least one inductor in a series LC circuit configuration operative to accept radio frequency (RF) power from the external charger, the series LC circuit configuration defining a first electrical node at a terminal of the at least one inductor and a second electrical node at a terminal of the at least one capacitor;
a bridge rectifier operative to generate a charging voltage at an output node of the bridge rectifier from an induced voltage provided by the inductive coupling element when magnetically coupled to the external charger to receive the RF power;
a series switch disposed between the first electrical node of the series LC circuit configuration and the bridge rectifier;
voltage regulation circuitry operative to regulate a level of the charging voltage generated at the output node of the bridge rectifier for charging the rechargeable battery; and
a coil clamp circuit configured to change the series switch to an OFF state based on an output of the voltage regulation circuitry to detune the inductive coupling element, whereby a high voltage condition is prevented from developing in the series LC circuit configuration of the inductive coupling element, and
wherein the external charger includes:
a clamp detector configured to detect clamping of the series LC circuit configuration due to at least one of: (i) detuning the series LC circuit configuration caused by opening the series switch, and (ii) assertion of a voltage control signal generated responsive to monitoring a target voltage level of the charging voltage generated by the bridge rectifier; and
a controller for monitoring a rate of occurrence of clamping at the series LC circuit configuration and, responsive to the monitoring of the rate of occurrence of clamping, for modifying a frequency of the RF power generated by the primary coil.

22. The system of claim 21, wherein the series switch is changed to the OFF state when the output of the voltage regulation circuitry is based on i.) a first voltage level, or ii.) a second voltage level greater than the first voltage level.

* * * * *